United States Patent [19]

Columbus et al.

[11] Patent Number: 5,070,884
[45] Date of Patent: Dec. 10, 1991

[54] NEEDLE DEVICE FOR SAFELY COLLECTING BLOOD OR INJECTING DRUGS

[75] Inventors: Richard L. Columbus, Rochester; Johannes J. Porte, Webster; Harvey J. Palmer, Lima, all of N.Y.

[73] Assignee: Eastman Kodak Company, Rochester, N.Y.

[21] Appl. No.: 481,838

[22] Filed: Feb. 20, 1990

Related U.S. Application Data

[63] Continuation-in-part of Ser. No. 323,459, Mar. 14, 1989, abandoned, Ser. No. 325,725, Mar. 20, 1989, Pat. No. 5,007,892, and Ser. No. 442,826, Nov. 29, 1989, abandoned.

[51] Int. Cl.⁵ .................................... A61B 5/00
[52] U.S. Cl. .................................... 128/760; 128/763; 604/403
[58] Field of Search .................. 128/760–766; 604/48, 49, 51, 192, 197, 198, 236, 263, 403, 411–413

[56] References Cited

U.S. PATENT DOCUMENTS

| | | | |
|---|---|---|---|
| 4,425,120 | 1/1984 | Sampson et al. | 604/198 |
| 4,492,634 | 1/1985 | Villa-Real | 128/763 |
| 4,631,057 | 12/1986 | Mitchell | 604/198 |
| 4,664,259 | 5/1987 | Landis | 206/365 |
| 4,737,144 | 4/1988 | Choksi | 604/198 |
| 4,801,295 | 1/1989 | Spencer | 604/198 |
| 4,850,374 | 7/1989 | Diaz-Ramos | 128/763 |
| 4,871,355 | 10/1989 | Kikkawa | 128/763 |
| 4,879,098 | 11/1989 | Oberhardt et al. | 128/763 |
| 4,892,107 | 1/1990 | Haber | 128/763 |
| 4,915,702 | 4/1990 | Haber | 128/763 |
| 4,957,637 | 9/1990 | Cornell | 604/411 |

FOREIGN PATENT DOCUMENTS 254246 8/1983 European Pat. Off. .

*Primary Examiner*—Stephen C. Pellegrino
*Assistant Examiner*—Michael Rafa
*Attorney, Agent, or Firm*—Dana M. Schmidt

[57] ABSTRACT

A needle device and method of use are disclosed, wherein the needle moves out of and into a protective housing, between two operative positions, one of which causes the housing to shield the needle. Each operative position includes releasable locking detents to temporarily hold the needle in one of those positions, the holding force of one being less than the other. A third position beyond the one that shields the needle in the housing is used to permanently lock the needle in the housing against accidental reuse. The needle device can be used with a blood collection container or a syringe drug delivery container, each one releasably mating with the device during use.

1 Claim, 6 Drawing Sheets

NEEDLE DEVICE FOR SAFELY COLLECTING BLOOD OR INJECTING DRUGS

Related Applications

This application is a continuation-in-part application of U.S. Ser. No. 323,459 filed on Mar. 14, 1989 entitled "Needle Housing With Retractable Needle" abandoned June 27, 1990 of U.S. Ser. No. 325,725 filed on Mar. 20, 1989 entitled "Phase Separation With Fixed Means Preventing Remixing", U.S. Pat. No. 5,007,892, Apr. 16, 1991 and of U.S. Ser. No. 442,826 filed on Nov. 29, 1989 entitled "Blood Collection Device" abandoned Sept. 11, 1990.

FIELD OF THE INVENTION

The invention is directed to a device used to collect blood from a mammal or deliver drugs thereto. When used to collect blood, the device acts to separate and collect the lighter phase, all in the same device.

BACKGROUND OF THE INVENTION

In needle devices, it is known to mount a needle on a frame that telescopes inside a sheath, the sheath extending around the needle to protect the needle except when in use. In such a device, the sheath and needle are moved from a needle-sheathed, nonuseful position, to a needle-unsheathed position in which the needle extends out through the aperture, as shown in, e.g., U.S. Pat. No. 4,425,120. However, the disadvantage of such a device is that there is no provision to prevent the needle from being reused. Even if it is moved back into said sheathed (protected) position, there is nothing that prevents it from being pushed out again where it can either intentionally or unintentionally inject a person. That is, the detent mechanism for keeping the needle sheathed is not a permanent disabling feature. This is understandable, since the device has to be unsheathed to be used. However, it means that no permanent disabling of the needle can be done after its first use.

Current methods of using needles, e.g., in drawing blood from or injecting drugs into a mammalian body, run substantial risks of contamination if a needle can be reused or restuck into another mammal, after having been used once. For this reason, standard health practice is to destroy each needle after one use. However, there is always the possibility, for standard syringe-type devices that do not provide adequate sheathing, that the needle will be stuck accidentally into another body before or while it is being destroyed. Furthermore, the snapping of a used needle, one method used to break them, can produce an aerosol that can be contaminating.

Because of the above problems, packaging has been provided to ensure that the needle is used only once and is not reusable when closed into its container. Thus, devices of the type shown in U.S. Pat. No. 4,664,259, allow a needle to pivot relative to a package through a slot, and when the package is pivoted back over the needle, the needle is captured by a hook to permanently prevent its reuse. Such a design, however, has several drawbacks. Most important is the fact that the sheathed position of the needle within the housing is the same whether or not the disabling mechanism is in place—that is, an operator cannot tell the status simply by looking at the housing. What has been needed, therefore, prior to this invention is a needle housing and locking mechanism for permanent disabling, that is operable using visual positioning that is unique to the needle status.

Yet another difficulty with devices such as are shown in U.S. Pat. No. 4,425,120 is that the relative movement of needle and housing, to expose or withdraw the needle, is a fairly complicated two-handed operation requiring both a twisting and a translation. There has been a need prior to this invention to provide needle housing devices that are not only protective, but can be operated with one hand.

Yet another problem with conventional phlebotomy devices is that they do not combine the collection, phase separation and automated dispensing of the serum all in one integrated device.

SUMMARY OF THE INVENTION

We have constructed a needle device and a method of use that meet the above-mentioned needs.

More specifically, in accord with a first aspect of the invention, there is provided a needle device for safely collecting blood or injecting drugs, the device comprising a needle and a housing for the needle, the housing including an aperture at one end; means slidably disposed within the housing for mounting the needle, the mounting means being shaped at one end to releasably mate with a container constructed to collect or deliver a liquid, the needle projecting into a mated container end sufficiently to penetrate the container when sufficient force is applied, means for releasably holding the mounting means in the housing in at least two positions, one of the positions locating the needle so as to be surrounded by the housing and the other position locating the needle to project through the aperture, and means for locking the needle and the mounting means permanently against further movement in the housing when the mounting means is moved from the one position to and past the other position to a third position, and further including either a blood collection container or a drug-injecting container preloaded with a drug, either container being releasably engagable with one of the needle ends within the mounting means and within the housing.

In accord with a second aspect of the invention, there is provided a needle device for safely collecting blood or delivering a liquid, the device comprising a needle and a housing for the needle, the housing including an aperture at one end; means slidably disposed within the housing for mounting the needle, the mounting means being shaped at one end to releasably mate with a container constructed to collect or deliver a liquid, the needle projecting into a mated container sufficiently to penetrate the container when sufficient force is applied, means for holding the mounting means in the housing in at least two positions, one of the positions locating the needle so as to be surrounded by the housing and the other position locating the needle to project through the aperture, the holding means being constructed to release the mounting means from the one position when a blood collection container is pushed into contact with the mounting means and the needle, and from the other position only in response to an effective force created by manually engaging and pulling the mounting means and the needle towards the one housing position, the effective force being greater than the force created by disengaging the container from the needle.

In accord with a third aspect of the invention, there is provided a needle device for safely collecting blood or injecting drugs, the device comprising a needle and a housing for the needle, the housing including an aperture at one end; means slidably disposed within the housing for mounting the needle, the mounting means being shaped at one end to releasably mate with a container constructed to collect or deliver a liquid, the needle projecting into a mated container end sufficiently to penetrate the container when sufficient force is applied, means for holding the mounting means in the housing in at least two positions, one of the positions locating the needle so as to be surrounded by the housing and the other position locating the needle to project through the aperture, and a button slidably mounted in a slot in the housing, the button including a portion inside the housing that engages the mounting means when the button is moved rearwardly from the other position to the one position.

In accord with a fourth aspect of the invention, there is provided a method for safely injecting a needle into a mammalian body to collect blood or inject a drug, using a needle device comprising a needle, a protective housing with an aperture, and means for mounting the needle to slide within the housing and in and out of the aperture. The method comprises the steps of: a) obtaining the needle device from a source of supply with the needle in a first position that is completely and protectively withdrawn into the housing, b) locating the needle device at an injection site on a mammalian body, c) pushing the needle axially without rotation, out of the first position to a releasably locked second position with the needle exposed, by pushing a container against the needle, the container being constructed to collect blood or deliver a drug, d) injecting the needle into the mammalian body and releasably injecting said needle into said container, e) collecting blood or injecting a drug through the needle, f) withdrawing the needle from the mammalian body, g) withdrawing the needle from the second position to the first position, and h) moving and permanently locking the needle to a third position different from the first and second positions.

In accord with a fifth aspect of the invention, there is provided a needle device similar to those described in aspects one through four, the device including control means for manually engaging the needle mounting means to slide it from a position where the needle is extended out through the aperture, to a position in which the needle is withdrawn in the housing. The device is improved in that the control means is disconnected from the needle mounting means and is free to slide towards the aperture without advancing the needle, and the control means includes a member that projects into contact with the needle mounting means as the control means is withdrawn away from the aperture, whereby the control means is effective to move the needle relative to the housing only in a withdrawal of the needle from the extended position to the withdrawn position, and inadvertent extensions of the needle out the aperture by accidental movement of the control means are not possible.

In accord with a sixth aspect of the invention, there is provided a multi-phase integral blood collection and separation device, comprising a first chamber for receiving and separating the liquid into at least two phases by spinning the chamber about an axis external to the chamber, the chamber including means for maintaining the phase separation after spinning;

collecting means for collecting the liquid, the collecting means including a needle constructed for penetrating the chamber;

means for protecting a user from being stuck by the needle when it is not penetrating the chamber;

a second chamber for collecting the lighter of at least two phases from the first chamber, the second chamber including a first aperture for obtaining the lighter phase from the second chamber;

and a valve means for controlling the flow of liquid from the first chamber to the second chamber.

In accord with a seventh aspect of the invention, there is provided a method of collecting whole blood and separating serum from the cells of the blood, comprising inserting a phlebotomy tube into a needle mount having a protective sheath slidable thereover, sliding the needle mount within the protective sheath until a) the needle extends out of the sheath and b) the needle has penetrated the tube, collecting blood in the tube, the tube including as composite parts thereof, a first chamber for receiving and separating the liquid into at least two phases by spinning the chamber about an axis external to the chamber, the chamber including means for maintaining the phase separation after spinning a second chamber for collecting the lighter of the at least two phases from the first chamber, the second chamber including a first aperture for recovering the lighter phase from the second chamber; and a valve means for controlling the flow of liquid from the first chamber to the second chamber in response to hydrostatic pressure;

removing the tube from the needle, spinning the tube in a centrifuge until the heavier cell phase is separated from the lighter serum phase, and removing the lighter phase into the second chamber by opening the valve.

Accordingly, it is an advantageous feature of the invention that a needle device is provided for blood collection or drug injection that, once used, is permanently locked in its protected position against reuse in a manner that readily demonstrates its status.

It is another advantageous feature of the invention that such a needle device and method of use are provided that allow for one-handed operation of the needle within the housing, at least for the withdrawal step after use, and optionally for both withdrawal and projection of the needle out of the housing.

It is yet another advantageous feature of the invention that such a needle device, when used to collect blood, does not allow improper coaction between collection container and needle until the needle is projected for injection into the patient.

It is still another related advantageous feature of the invention that such a needle device, when used to collect blood, resists withdrawal of the needle into its housing until after all collection containers are removed.

It is a further advantageous feature of the invention that the engagement and disengagement of the needle with a blood collection container is coordinated with the desired movement of the needle in and out of the housing.

It is yet a further advantageous feature of the invention that a phlebotomy tube is provided for use with a user-protected syringe, that allows the separation of serum and withdrawal of the serum into its own chamber, to occur within that same tube used for the collection.

Still a further advantageous feature of the invention is the provision of a handle that is useful repeatedly with the above-noted tubes.

Other advantageous features will become apparent upon reference to the following Detailed Description of the Preferred Embodiments, when read in light of the attached drawings.

DESCRIPTION OF THE PREFERRED EMBODIMENTS

Figure 1:
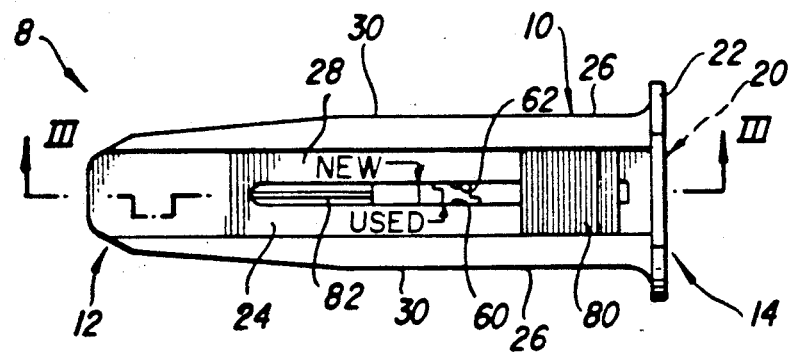
FIG. 1 is a plan view of a needle device constructed in accordance with the invention.

The invention is hereinafter described with respect to preferred embodiments, wherein the needle device cooperates and is mated with either a blood collection container or a syringe for delivering a drug to a human. In addition, it is useful regardless of what liquid is collected or the particular construction of the collection container, and in the case of a syringe, it is useful regardless of what liquid is being delivered or the construction of the syringe. It is further useful in treating non-human animals.

Turning to FIGS. 1-5, a needle device 8 constructed as per the invention comprises a housing 10 having a front, tapered end 12 and an open rear end 14. The entire housing is hollow, with end 12 being apertured at 16 on the axis 17 of the housing, FIGS. 3A and 3B. The taper at end 12 is at an angle alpha designed to allow the housing (and needle, when extended) to enter the skin at an angle that is reduced compared to the angle required if end 12 were blunt, as is more clearly shown in FIG. 10. End 14 is open at 20, FIG. 2, to receive either a mating drug-delivering syringe container or a blood collection container. A gripping flange 22 is provided at the terminal end surface.

Figure 2:
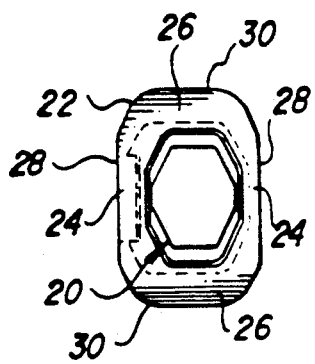
FIG. 2 is an end elevation view of the device of FIG. 1.

Housing 10 has two pairs of opposing sides 24, 26, FIG. 2. These are provided with flats 28, 30, respectively, the flats of an opposing pair being preferably parallel. Such flats prevent the housing from rolling when the device is on a horizontal surface.

Figure 3A:
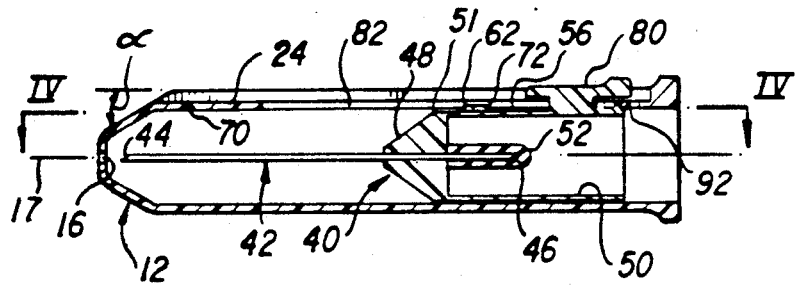
FIGS. 3A and 3B are two section views taken generally along the line III—III of FIG. 1, but illustrating two alternative embodiments.
Figure 3B:
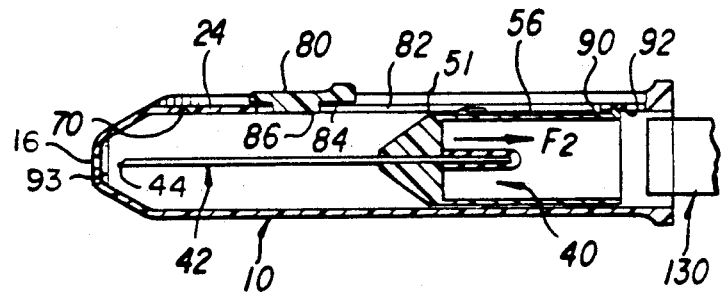

As is clearly shown in FIG. 3A or 3B, housing 10 is preferably entirely hollow, having slidably mounted therein mounting means 40 and its needle 42. Needle 42 has a skin-penetrating end 44 and a container-penetrating end 46. Means 40 comprise a front, cone-shaped member 48 shaped to mate with tapered end 12 of the housing, and a rear cylinder 50 shaped to matingly engage a blood collection container or a syringe container. End 46 of needle 42 fixedly projects through member 48 and part way into cylinder 50. Optionally, a boot 52 is mounted over end 46, provided from a self-sealing elastomer, to ensure that any body fluids that might spill out of end 46 are contained within the boot. Boot 52 is also effective in reducing the risk of accidental pricking of a finger that might get put into open end 20.

Figure 4:
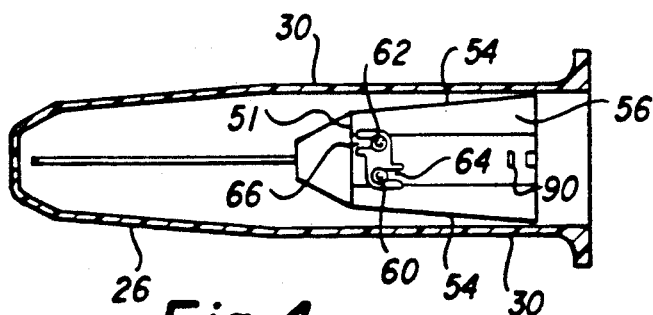
FIG. 4 is a section view taken generally along the line IV—IV of FIG. 3.

Cylinder 50 is preferably tapered at side surfaces 54 when seen in one elevational direction, FIG. 4, to allow a conforming fit to a preferred taper to walls 26 of housing 10.

One of the other walls 56 of cylinder 50 joins front member 48 at an indicia edge 51, FIGS. 3A and 3B and FIG. 4. Wall 56 includes means for releasably locking mounting means 40 into one of two positions within housing 10—a first position with needle 42 completely withdrawn, FIGS. 3A or 3B, and a second position with the needle fully extended, FIG. 5. Preferably, such releasable locking means comprise one and most preferably, two detents 60, 62, FIG. 4, in wall 56 that cooperate with a matching slot 70 and 72 in one wall 24 of housing 10, FIGS. 3A and 3B. Detents 60 and 62 are preferably mounted on the end of cantilever arms 64 and 66, respectively, FIG. 4, each constructed with a thickness and of a material to provide a predetermined resistance force before its detent can be elastically forced out of its slot, as is well-known. Two arms are preferred to allow the resistance force of one arm to be greater than the other. If no difference is needed, one lever arm suffices.

A manually operated button 80 is slidably mounted in a slot 82 in wall 24 of housing 10, as is best shown in FIG. 3A or 3B. Button 80 either engages mounting means 40 when it is moved rearwardly by being integrally *attached* to mounting means 40, FIG. 3A, or it is free-floating within slot 82 and engages means 40 during rearward movement only, FIG. 3B, because of projection 90 on mounting means 40 at end 92 thereof, FIGS. 3B and 5. In the latter case, surface 84 of button 80, under wall 24, has an edge 86 that projects down far enough to catch projection 90, as is more clearly shown in FIG. 6, when button 80 is moved rearwardly, discussed in greater detail hereinafter.

FIG. 3B also illustrates the optional use of a cover member 93 that is disposed between aperture 16 and needle end 44. Member 93 acts as a wipe when the needle is *withdrawn*, and thus is an absorbent material such as paper or a foam. By such means, the risk of a drop of blood floating around inside the device is minimized.

Figure 6:
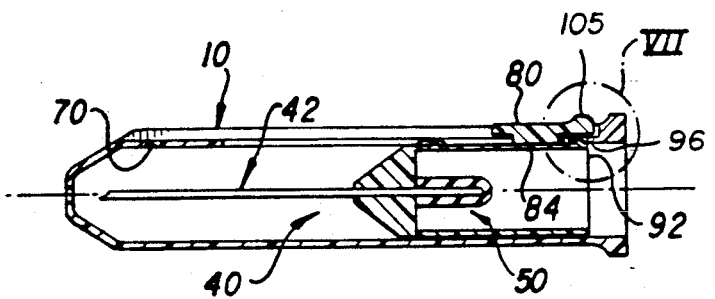
FIG. 6 is a section view similar to that of FIG. 3, but illustrating the device in its permanently locked position.
Figure 7:
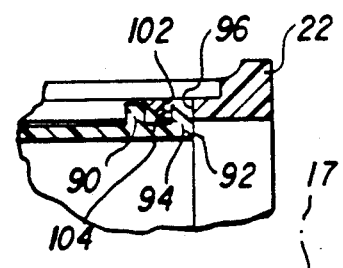
FIG. 7 is an enlarged section view of the portion in FIG. 6 circled as "VII", the manual button having been removed for clarity.
Figure 11:
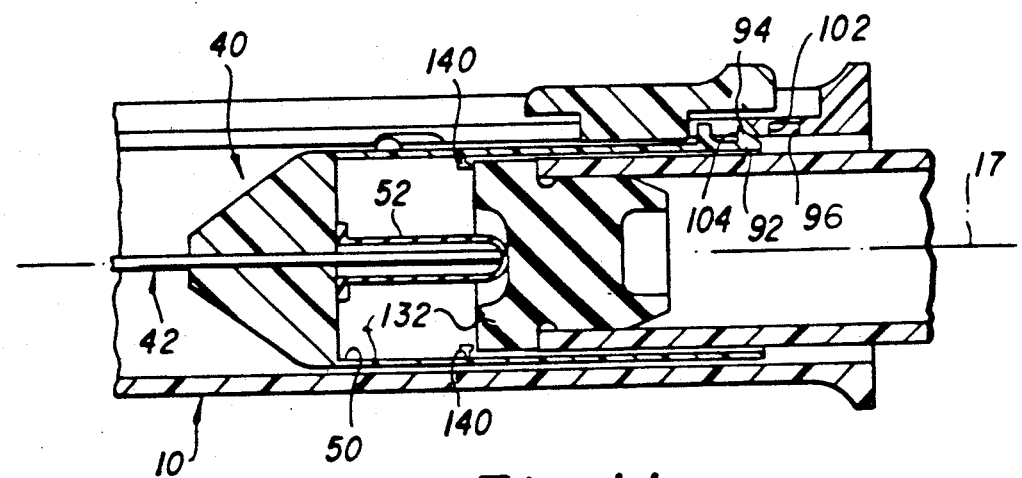
FIG. 11 is a fragmentary section view similar to that of FIGS. 3 and 9, but illustrating an alternate embodiment.

As is more clearly shown in FIGS. 7 and 11, end 92 of mounting means 40 also includes locking detent 94 for permanently engaging housing 10 when means 40 is moved into a third position rearwardly beyond that shown in FIGS. 3A and 3B. Cooperating with detent 94 is an aperture 96 built into wall 24 adjacent to flange 22, FIG. 7. To render it easy for locking detent 94 to "jump out of" slot 82, FIG. 11, and into aperture 96, FIG. 7, the end surface 100 of slot 82 is chamfered, FIG. 8, as is the rear edge of projection 94. However, the forward surface 102 of aperture 96 and the forward edge 104 of detent 94 are generally perpendicular to axis 17 of housing 10, to prevent unlocking of the two, once the third position of FIGS. 6 and 7 is reached.

To render the locking feature invisible to the user, and also inaccessible, rear portion 105 of button 80 preferably extends over aperture 96, FIG. 6.

Figure 5:
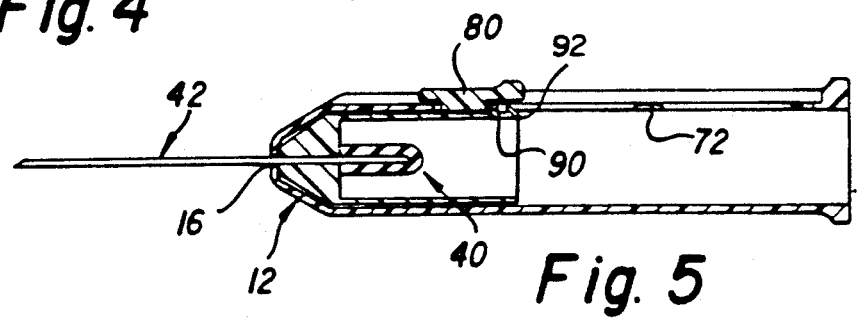
FIG. 5 is a section view similar to that of FIG. 3, but illustrating the device with the needle in its extended position.

Thus, the first withdrawn position shown in FIGS. 3A and 3B is in between the extended position of FIG. 5 and the locked position of FIG. 6. This permanently locked position is the final position of the needle device after it is used once. To readily indicate such, indicia can be placed on wall surface 24, FIG. 1, which show an arrow lined up with the front edge 51 of mounting means 40 when the device is unused, and a "used" arrow further back which will line up with edge 51 when means 40 is in the third, locked position of FIG. 6. Alternatively, other indicia formats can be used to help distinguish the device being in the third position rather than the first position.

Whether button 80 is integrally attached to mounting means 40, or is free to slide independent thereof, depends upon the usage desired of the device. A preferred usage of the integrally attached version, FIG. 3A, is one in which there is no reason to be concerned about premature injection of the needle into a mated collection container or syringe delivery container. That is, the presence of button 80 invites the user to place a thumb thereon while the mating container is being loaded into cylinder 50. Thus, if button 80 is integral with mounting means 40, it is most likely penetration of the container by needle end 46 will occur while needle end 44 is still sheathed within housing 10.

Figure 8:
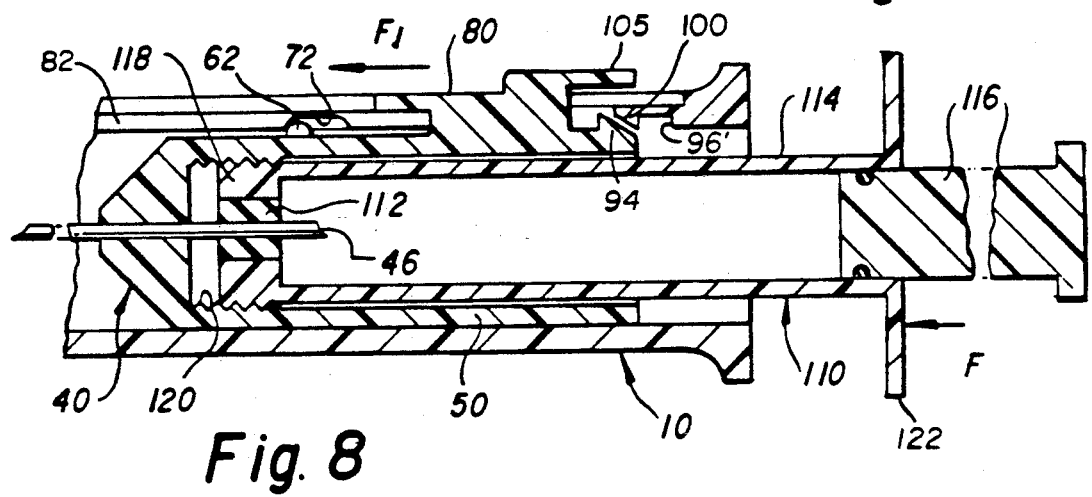
FIG. 8 is a fragmentary section view similar to that of FIG. 3, illustrating the device when used with a drug delivery container.

Accordingly, a highly preferred use of the integrally attached button 80, FIG. 3A, is that illustrated in FIG. 8. A syringe drug delivery container 110 is inserted into housing 50, so that needle end 46 preferably penetrates septum 112 of container 110 before detent 62 moves out of slot 72. Container 110 comprises a conventional syringe cylinder 114 that holds septum 112, and any suitable plunger or piston 116. Cylinder 114 can be provided with male threads 118 to cooperate with female threads 120 of cylinder 50, as shown, or simply be slid into place. The threaded connection is preferred, since the screwing motion while button 80 is held down, will aid in puncturing septum 112 without having to exert considerable force F on flange 122 of cylinder 114, and thus accidentally depress piston 116. When drug injection is ready, the operator simply applies to button 80, a force $F_1$ that is sufficient to override the force holding detent 62 in slot 72, and mounting means 40 plus the syringe assembly slide forward to allow needle end 46 to penetrate the mammal that is to receive the drug. Thus, the insertion of the needle device of FIG. 8 into the mammal can be done with one hand—the fingers grip housing 10 and the thumb pushes forward button 80. Thereafter, piston 116 is depressed to inject the drug. The threaded connection of container 110 to mounting means 40 is preferably temporary, so that container 110 can be unscrewed and removed after drug delivery.

As with the embodiment shown in FIG. 6, rear portion 105 of button 80 covers the locking portions 94 and 96. Alternatively, the aperture portion can be formed only as a depression 96' as shown, FIG. 8, instead of a penetrating aperture.

However, if the container to be used with the needle device is a blood collection container, then preferably button 80 is free-floating as shown in FIG. 3B. It is precisely because the user may hold button 80 down while inserting a collection container 130, that it should be free-floating. Otherwise, premature needle penetration of the container 130, which preferably has a partial vacuum, may occur.

In this embodiment, detent 62 engages slot 72 with a force having an axial component $F_2$, FIG. 3B, that is a function of the dimensions of detent 62 and slot 72, and the materials of the detent lever arm. As container 130 is pushed against boot 52 and needle end 46, FIG. 9, there is a force $F_3$ (not shown) that will be needed to cause needle end 46 to penetrate septum 132 of container 130. Conventionally, evacuated containers 130 are constructed so that such force $F_3$ is for a 10 mm size of container 130, between about 1 (0.45 Kgm) and 3 lbs. (1.36 Kgm). See, e.g., Percarpio, *Transaction of the ASME*, Vol. 102, p. 242-246 (April 1980). Since detent 62 and slot 72 (FIG. 8) are to disengage before such a force is reached, to allow needle end 44 to protrude out of housing 10 and into the mammal skin S, FIG. 9, the construction of detent 62 and slot 72 is such as to release at a force $F_2+$ that is just greater than $F_2$ and less than 0.45 Kgm (1 lb.), e.g., at a force of 0.225 Kgm (0.5 lb.). The selection of detent sizes and materials to accomplish such a value of $F_2$ are known to the skilled engineer. The force of engagement $F_2$ should be greater than negligible, to prevent accidental premature extension of the needle.

Figure 9:
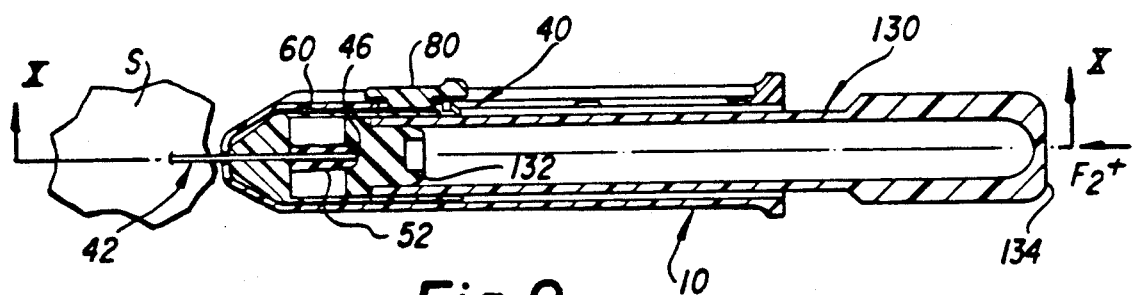
FIG. 9 is a section view similar to that of FIG. 5, but illustrating the device in one stage of its use with a blood collection container.

As a result, application of force $F_2+$, FIG. 9, to end 134 slides container 130 and mounting means 40 (and button 80) into the extended position of housing 10, but without penetrating needle 42 into container 130, thus penetrating the skin S. The taper of end 12 provides for the shallow angle of insertion alpha, as shown. The longer the taper, the shallower this angle can be.

When mounting means 40 is in the position shown in FIG. 9, detent 60 engages slot 70 of housing 10.

Figure 10:
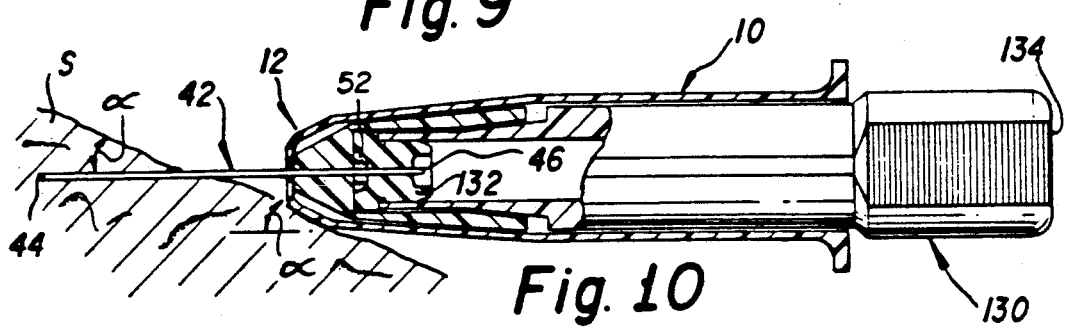
FIG. 10 is a section view taken generally along the line X—X of FIG. 9, illustrating, however, the container with the needle penetrating its stopper at one end and the skin at the other.

Upon the application of force $F_3$, noted above, to end 134 of container 130, container 130 slides further forward, FIG. 10, to allow puncture of septum 132 and the immediate draw of blood from the mammal.

To aid in ensuring that mounting means 40 moves out of its first position, FIG. 3B and into the second position, FIG. 9, without needle penetration of septum 132, break-away tabs 140 can be optionally included, FIG. 11, on the inside surface of cylinder 50. The tabs are located to resist penetration of the septum by the needle when force $F_2+$ is applied. These can be molded in place, or caused to be formed by punching them inwardly. However formed, when force $F_3$ is applied, they break off to allow needle penetration.

Figure 12:
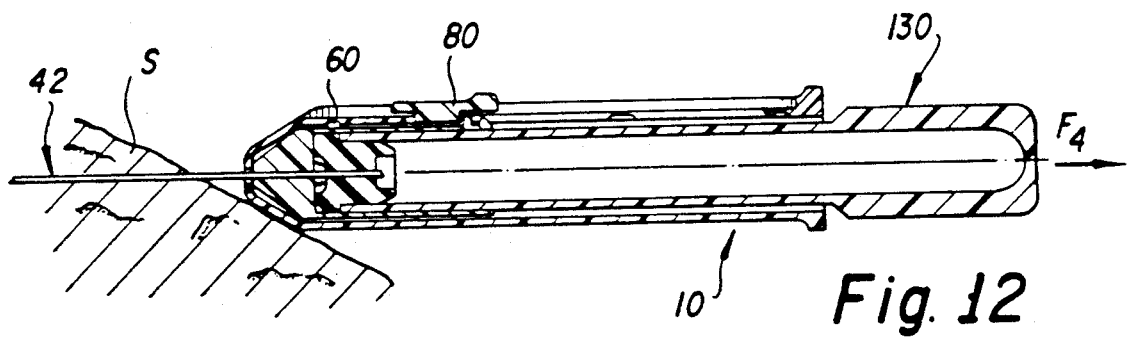
FIG. 12 is a section view similar to that of FIG. 9, showing a blood collection container just prior to its removal.

It is conventional practice to remove container 130 when full, and insert yet another one, of the same or different size or volume, while still keeping needle 42 in the mammal. In this invention, such additional containers are constructed to mate with cylinder 50, regardless of their volumes. Boot 52 returns to the position shown in FIGS. 9 or 13, and reseals, when a container is withdrawn, thus preventing blood from spilling. However, it is essential in such cases that the force $F_4$ used to pull container 130 out, be insufficient to release detent 60 from its slot 70 of housing 10, FIG. 12. The materials and dimensions used to construct detent 60, its lever arm, and slot 70 are adjusted accordingly. Because such container withdrawal forces are conventionally less than 0.45 Kgm (1 lb.) for a 10 mm container (Percarpio, noted above), the axial force $F_5$ (not shown) needed to disengage detent 60 from slot 70 is greater than 0.45 Kgm (1 lb.), for example, 0.9 Kgm to 1.36 Kgm (2 to 3 lbs.).

Figure 13:
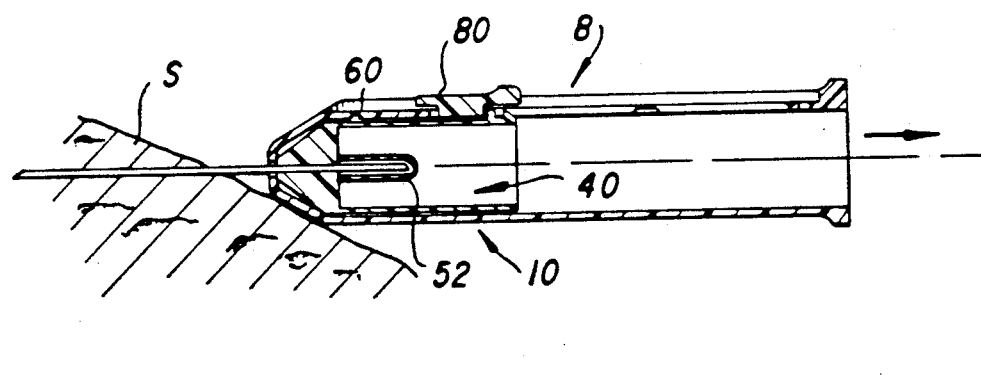
FIG. 13 is the same section view as FIG. 12 but with the container fully disengaged.
Figure 13:
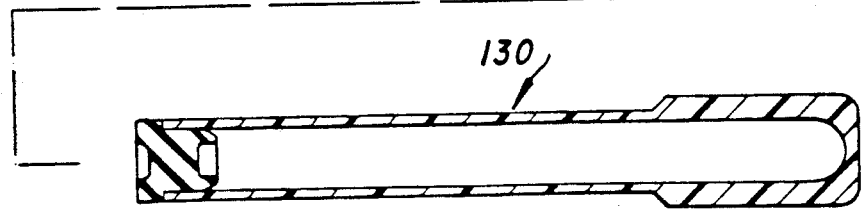

The result is the removal of container 130, FIG. 13, with needle device 8 still inserted into the mammal.

When blood collection is complete, preferably the operator simply applies a thumb to button 80, while holding housing 10 stationary, and forcefully withdraws it and the mounting means 40 now engaged by the button, with a force greater than the disengaging force $F_5$ of detent 60 and slot 70, noted above. This simultaneously withdraws the needle from the mammal and pulls means 40 to its withdrawn position. Since that disengaging force is preferably 0.9 to 1.36 Kgm (2 to 3 lbs.), such can be readily done with a single hand. Most preferably, the rearward movement of thumb, button 80, and mounting means 40 is continued until means 40 locks into its third, most rearward position, FIGS. 6 and 7. At this position, the device is locked permanently against reuse, apart from deliberate disassembly of the device, a task that is difficult at best.

Alternatively, although it is not preferred, the needle 42 can be withdrawn from skin S prior to the movement of cylinder 50 and means 40 from the needle-extended position to the third, completely-withdrawn-and-locked, position.

Figure 14:
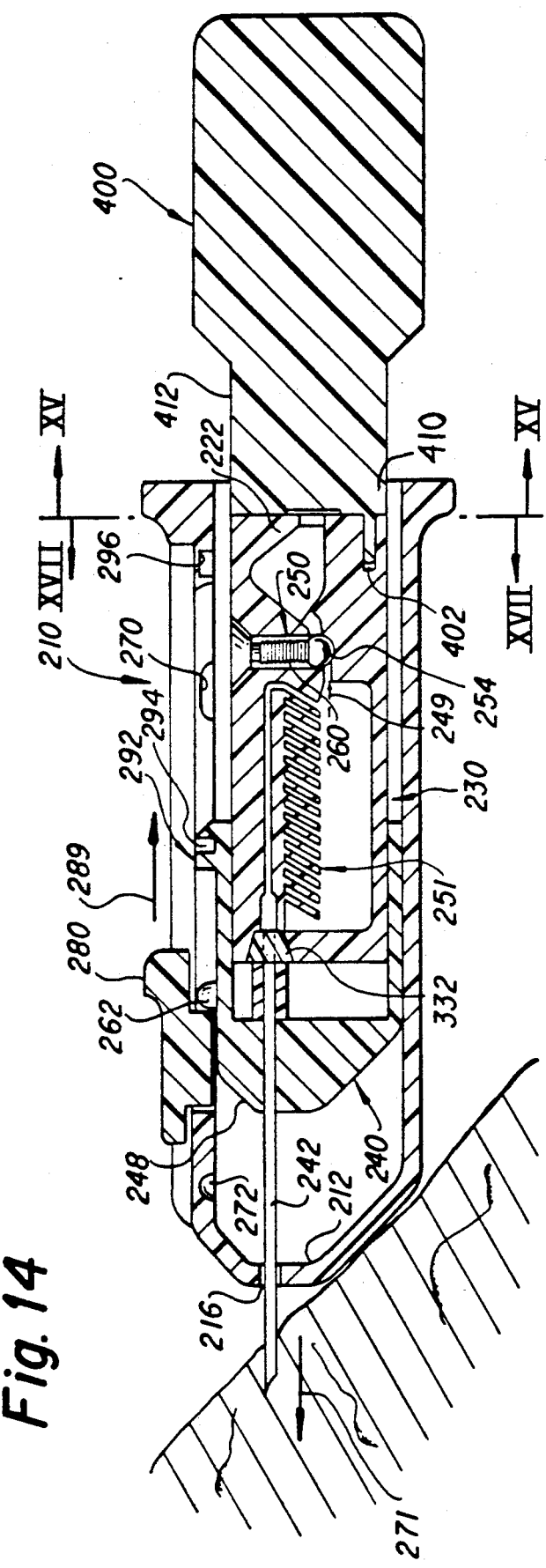
FIG. 14 is a section view similar to that of FIG. 9, but illustrating an alternate embodiment of the phlebotomy tube.
Figure 18:
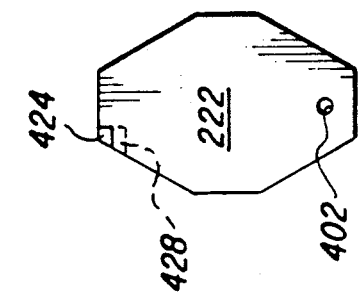
FIG. 18 is a fragmentary side elevational view of the handle-engaging end of the tube shown in FIG. 17.
Figure 17:
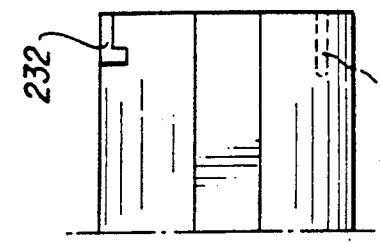
FIG. 17 is a section view taken generally along the line XVII—XVII of FIG. 14.
Figure 16:
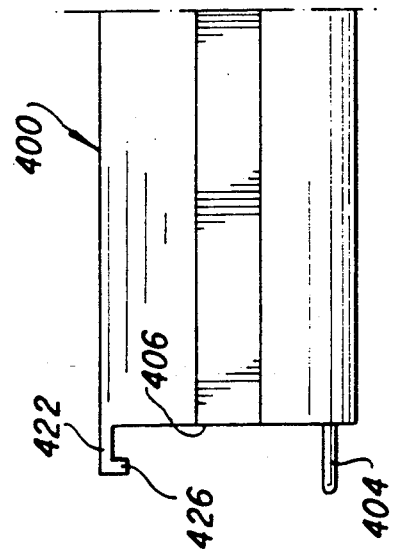
FIG. 16 is a fragmentary side elevational view of the handle shown in FIG. 15.
Figure 15:
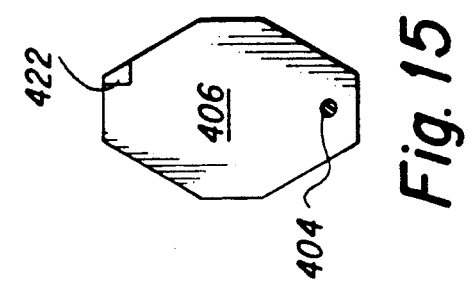
FIG. 15 is a section view taken generally along the line XV—XV of FIG. 14.
Figure 19:
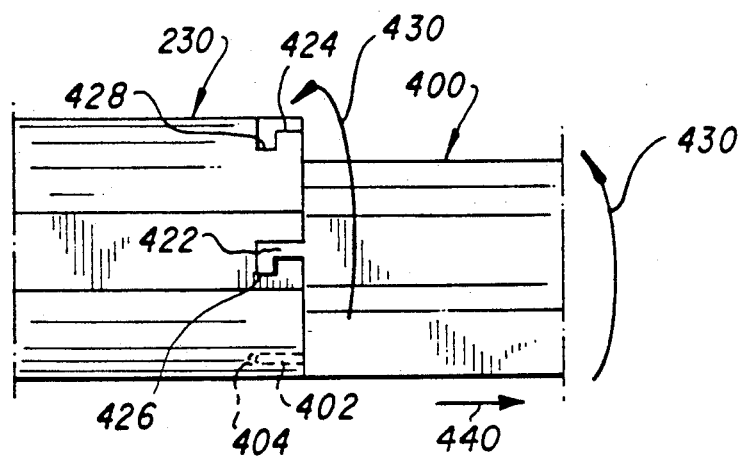
FIG. 19 is a fragmentary side elevational view of the tube of FIGS. 17 and 18 as it engages the handle of FIGS. 15 and 16.
Figure 20:
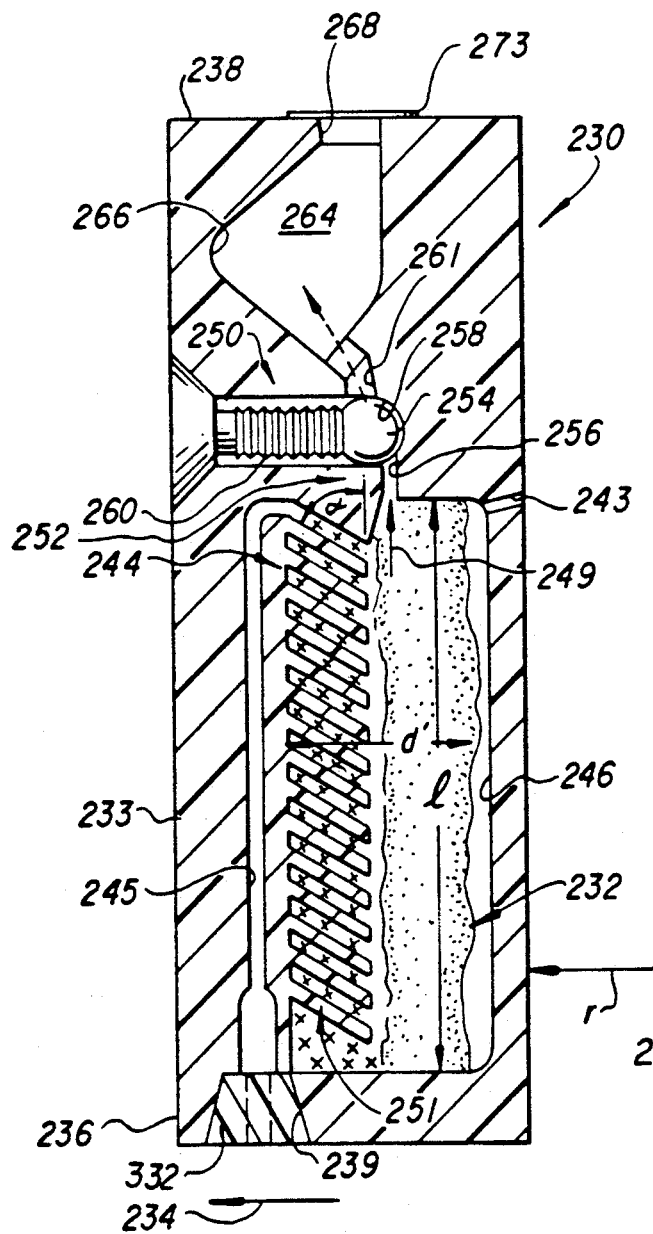
FIG. 20 is an enlarged section view of the tube of FIG. 14, illustrating its use for serum separation.

When the needle device of the invention is used for blood collection, an improved phlebotomy tube can be used that has built into it, the capability of serum separation using centrifugal separation forces that are lower than with conventional devices. FIGS. 14 and 20 illustrate such a tube, and how it is integrated into the syringe of this invention.

More specifically, tube 230 generally fits within a needle-mounting means 240, which in turn slides within a protective housing 210 in the manner of the previous embodiments. That is, releasable locking detents such as detent 262 act to engage and disengage with slots 272 and 270, respectively, to allow the needle mount to be pushed out through aperture 216 and into the patient, arrow 271, as shown, FIG. 14, by pushing tube 230 against the needle 242 without causing penetration of septum 332. However, further pushing of the tube will both cause needle penetration of the septum, end 248 of means 240 to sit against end 212 of housing 210, and the desired patient penetration. After blood collection is complete, free-floating control button 280 is effective as with the previous embodiments to pull mounting means 240 out of end 212 and the patient, arrow 289, since the button presses against end 292 of mounting means 240. Projection 294 of end 292 then irretrievably locks with locking detent 296 of housing 210, as in the previous embodiments, to prevent needle 242 from being re-extended out through aperture 216.

Tube 230 is then pulled out of mounting means 240 using handle 400 described hereinafter, which is removed from the tube. The remaining features of tube 230 are those that differ from the tubes of the previous embodiments, and which allow the blood separation to occur within tube 230 during subsequent processing (not shown).

More specifically, tube 230, FIG. 20, is constructed with a chamber 232 for phase separation by centrifugation, that has its long dimension l oriented perpendicular, not parallel, to the direction of centrifugal force CF, arrow 234, and with a specially constructed valve 250. Chamber 232 is defined by a body member 233 having a blood intake end 236 and an opposite, serum-removal end 238. Chamber 232 extends from end 236 to a delivery passageway 256. End 236 has an intake aperture 239 filled with a conventional septum 332, chamber 232 being either vented at 243 or pre-evacuated to assist in blood intake. Aperture 239 allows entrance of whole blood via a passageway 245 to chamber 232. The width "d" of chamber 232 is one of the shorter dimensions, enough blood being drawn in to fill to about the depth d'. Sidewall 244 of chamber 232 is the sidewall against which the heavier blood cells collect, whereas opposite sidewall 246 is adjacent the lighter serum fraction, during centrifugation. Thus, dimension d' extends from the lighter phase into the heavier phase.

Optionally, fixed porous mechanical means, such as baffles 251, can be positioned along wall 244 so as to be disposed in the blood cells. Such means act to retain the heavier phase from remixing when the lighter, serum phase is drawn off in the direction of arrow 249. The plates of the baffles are inclined at an angle alpha that resists remixing forces when flow occurs out of chamber 232 in the direction of arrow 249. Preferably, this angle is a value that is between about 30° C. and about 120°, most preferably about 60°. Preferably, the distance between the individual plates of baffles 251 is between about 0.018 cm and about 0.10 cm, most preferably about 0.025 cm. The thickness of each plate is not critical, so long as a significant number of such plates are present as will create the needed volume between them to collect the blood cells.

Valve 250 is disposed at an end 252 of chamber 232 intermediate ends 236 and 238, positioned to draw off separated plasma or serum, and lymphocytes. Most importantly, valve 250 is constructed to open only in response to a hydraulic head of force, and not to the effects of force CF, regardless of the magnitude of the latter. To this end, valve 250 is preferably a ball check valve with a ball 254 positioned downstream of passageway 256 at chamber end 252. Ball 254 seats against a hemispherical seat 258, and is biased by a spring 260 aligned to act in a direction that is generally parallel to the direction of force CF. The spring constant is selected to allow ball 254 to unseat from seat 258 only when a hydrostatic head of pressure of serum is applied to it in excess of the force exerted by force CF, arrow 234.

Passageway 261 is constructed adjacent seat 258, to carry off the liquid when valve 250 opens. Passageway 261 joins a chamber or compartment 264 sized to receive substantially all the liquid that exits chamber 232 via valve 250. Chamber 264 has a deep well portion 266 designed to collect lymphocytes, and a large opening 268 adapted to allow a pipette access to chamber 264 generally and to well portion 266 in particular. A cover 273 is removably sealed over opening 268 except when access of the pipette or other removal means is desired.

Recess 274 not only holds spring 260, but it also acts as a trap. The function of the trap is to collect the few red blood cells that will gather prior to and during centrifuging, in passageway 256, allowing only desired serum, or plasma and lymphocytes, to pass into chamber 264.

Tube 230 can be assembled as two plates, using a foil layer to achieve a seal that will allow a vacuum to be drawn, e.g., using vent 243.

Such a device 230 can be spun in any convenient centrifuge, not shown, where the long dimension l is generally parallel to the spin axis 276. Preferred spin radii are about 2.5 cm, although a wide variety can be used.

The method of blood separating, using device 230, will be readily apparent from the preceding discussion. Whole blood is drawn into chamber 232 by, e.g., a needle that penetrates septum 332. Device 230 is then spun about axis 276. However, the speed of rotation that is selected preferably is slow—a speed producing no greater than 400 g's centrifugal force, and most preferably no greater than 30 g's. The reason is that device 230 is capable of achieving phase separation at such forces, using 2 mL of liquid, in less than 2 minutes, and in some cases less than 1 minute, due to the (relatively) short distance (about d'/2) that the blood cells have to traverse to be separated. The serum, or plasma and lymphocytes, can be separated in less than 1 minute if the centrifugal force is about 150 g's or greater, there being little separation time enhancement occuring at forces above 400 g's. A separation force of only 30 g's will produce complete phase separation in less than 8 minutes, for example, 5.5 minutes. As a comparative example, as described in U.S. Pat. No. 4,818,418 the conditions achieved using a conventional Ficol-Pague/Percoll as an additive and a force of 400 g's is effective to achieve separation only after 30 minutes.

Whatever centrifugal force that is selected, after serum or plasma separation occurs the lighter phase is then drawn off the stacked liquid in chamber 232, by opening valve 250. This occurs as follows: spring 260 has a spring constant as noted that is pre-selected to resist movement of ball 254 until a certain head of pressure builds up against ball 254. The increased head of pressure occurs by increasing the centrifugal force a factor, for example 50%, above the force used to achieve phase separation. Preferably, the speed of rotation is increased a corresponding amount. Since the serum and blood cells are relatively incompressible against wall 244, the increase in centrifugal force CF translates into an increased force in the direction of arrow 249, which overcomes the spring constant of spring 260, and the valve opens.

The spring constant of spring 260 is selected as follows: It is selected so that valve 250 will not open at the first centrifugal force $CF_1$ used to achieve phase separation. Moreover, it is strong enough to prevent valve opening even in the presence of the higher centrifugal speed $CF_2$ used to create a head of pressure on the valve, in the absence of any liquid pressing on ball 254. However, because ball 254 has a surface that is included at a non-90° angle to the force of arrow 249, ball 254 will incur a force parallel to arrow 234 due to a liquid head of pressure $\Delta P$ generated in the direction of arrow 249, caused by centrifugal force $CF_2$. (The component of $\Delta P$ that is parallel to $CF_2$ is hereinafter designated $\Delta P_{CF}$.) That is, the selected spring constant provides for a force greater than the force generated by $CF_2$ alone, but less than ($CF_2 + \Delta P_{CF}$). When all of the lighter phase liquid has transferred to chamber 264, there no longer is a liquid head of pressure creating a force $\Delta P_{CF}$, and valve 250 closes automatically, even in the face of a centrifugal force $CF_2$.

Figure 21:
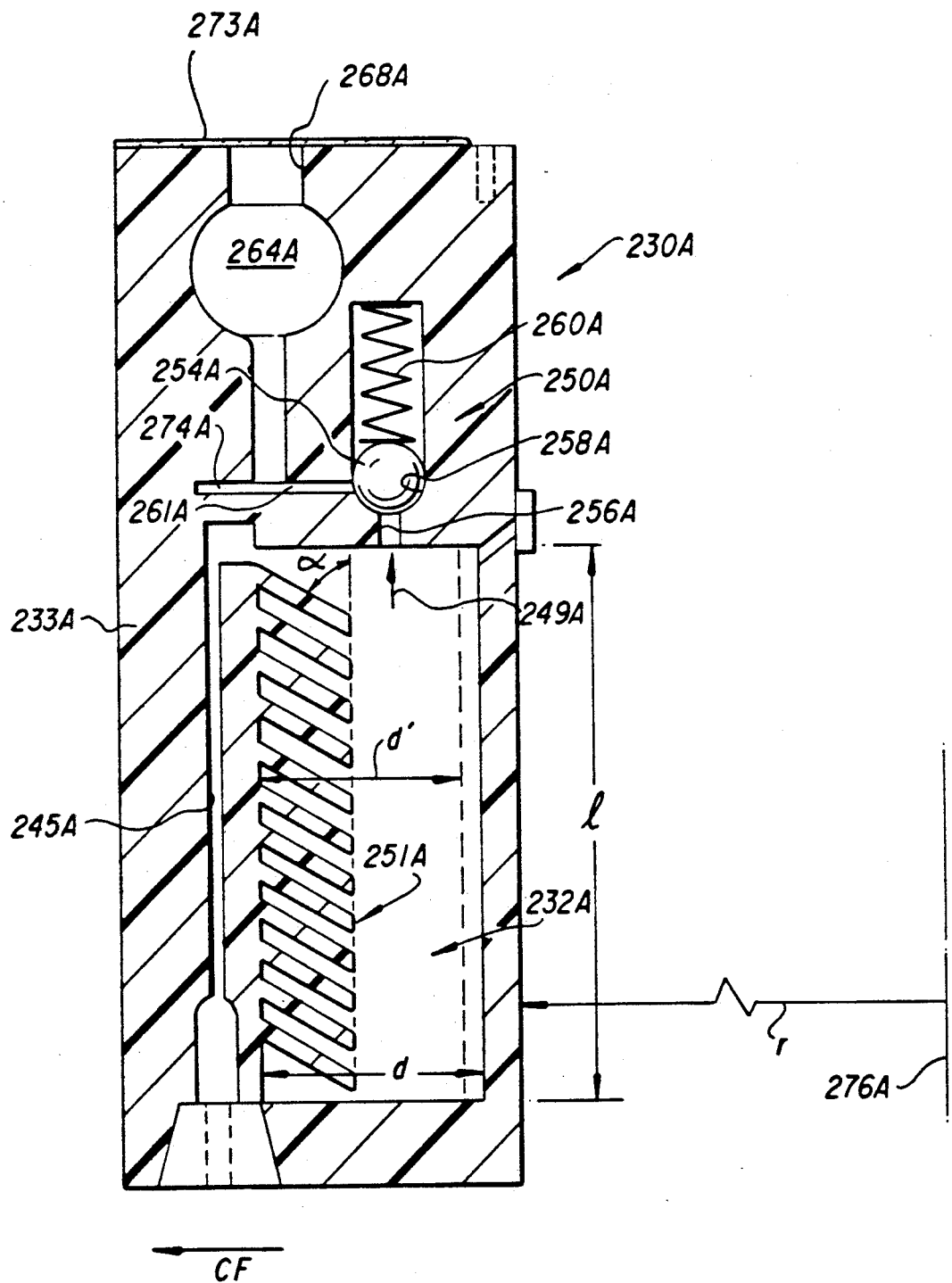
FIG. 21 is a section view of yet another embodiment of a phlebotomy tube that is useful in the environment of FIG. 14.

It is not essential that the valve operate on an axis that is parallel to the centrifugal force. In fact, it can be mounted on an axis that is perpendicular, to ensure the ball will not unseat due to centrifugal force CF alone, FIG. 21. Parts similar to those previously described bear the same reference numeral, to which the distinguishing suffix A has been appended.

Thus, tube 230A comprises a body 233A having a chamber 232A, passageway 245A supplying blood thereto as before. Baffles 251A can be included to retain the heavier blood cells, and passageway 256A allows removal of the lighter phases such as lymphocytes and plasma, into covered chamber or compartment 264A, from chamber 232A, using valve 250A. The long dimension l of chamber 232A is parallel to spin axis 276A. However, in this embodiment spring 260A is oriented to be perpendicular to the direction of centrifugal force CF. The spring constant of spring 260A is selected so that ball 254A opens only in response to a liquid head of pressure, and not in response to the centrifugal force. When ball 254A lifts off seat 258A, the lighter phases pour into chamber 264A. In this embodiment, a trap recess 274A extends off of passageway 261A to trap any blood cells caught in passageway 256A prior to phase separation.

The contents of chamber 264A, such as lymphocytes and plasma, are then aspirated out, by removing cover 273A.

The valve for automatic removal of the lighter phase need not be a ball valve, to respond only to the liquid head of pressure. Any valve can be used, if it is constructed to resist forces other than this head of pressure.

A removable and reusable handle 400 is preferably mounted on end 222, FIG. 14, of the tube 230, by reason of the features shown in FIGS. 15-19 in detail. This is the handle described and claimed in commonly owned U.S. Pat. No. 5,050,617 entitled "Removable Handle and Means for Attachment to a Syringe or Phlebotomy Device". That is, end 222 is provided with a recess 402, FIGS. 14 and 17, sized to receive a stud 404 projecting from mating end 406 of handle 400, FIGS. 14-16. Stud 404 and aperture 402 are preferably located adjacent one edge 410 of the mating parts, FIG. 14. Adjacent an edge 412 opposite to edge 410, a bayonet-type latch is provided on the mating parts, comprising a tongue 422 extending, for example, from handle 400, which slips into a mating latch groove 424 formed in end 222 of tube 230. End 426 of tongue 422 projects into a recess 428 of groove 424, so that when handle 400 is swiveled about stud 404, FIG. 19, arrows 430, tongue 422 will engage groove 424 and end 426 seats in recess 428 to prevent separation of the handle by translation movement of the handle away from tube 230 along the tube's axis. As latched, handle 400 is securely attached for operator movement of tubes 230 or 230A into and out of the needle device of the invention. However, if handle 400 is rotated opposite to the direction of arrows 430, tongue 422 becomes disengaged from groove 424, and handle 400 can be pulled away from tube 230, arrow 440.

Handle 400 has several advantages stemming from its construction. When it is fully latched to tube 230 or 230A, the latching is a positive engagement that cannot slip, as some frictional engagements are capable of doing. Furthermore, the latched and unlatched configurations are, by reason of their different axial alignments, clearly distinguishable one from the other (compare FIGS. 14 and 19), so that the user knows immediately which situation is present.

The invention has been described in detail with particular reference to preferred embodiments thereof, but it will be understood that variations and modifications can be effected within the spirit and scope of the invention.

What is claimed is:

1. A method of collecting whole blood and separating serum from the cells of the blood, comprising
    inserting a phlebotomy tube into a needle mount having a protective sheath slidable thereover,
    sliding said needle mount within said protective sheath until a) said needle extends out of said sheath and b) said needle has penetrated said tube,
    collecting blood in said tube, said tube including as composite parts thereof, a first chamber for receiving and separating the liquid into at least two phases by spinning the chamber about an axis external to said chamber, said chamber including means for maintaining said phase separation after spinning, a second chamber for collecting the lighter of said at least two phases from said first chamber, said second chamber including a first aperture for recovering said lighter phase from said first chamber and a valve means for controlling the flow of liquid from said first chamber to said second chamber in response to hydrostatic pressure;
    removing said tube from said needle,
    spinning said tube in a centrifuge until the heavier cell phase is separated from the lighter serum phase,
    and removing said lighter phase into said second chamber by increasing the spinning forces sufficiently above the speed used to separate the phases to force said valve to open due to an increased hydrostatic head of pressure.

* * * * *